United States Patent [19]

Block et al.

[11] Patent Number: 5,500,428
[45] Date of Patent: Mar. 19, 1996

[54] FURYL-SUBSTITUTED PURINES AND ADENOSINE ANTAGONISTS

[75] Inventors: Michael H. Block, Congleton; Alison Harrison, Broken Cross; Rodney B. Hargreaves, Poynton, all of England

[73] Assignee: Imperial Chemical Industries PLC, London, England

[21] Appl. No.: 181,202

[22] Filed: Jan. 13, 1994

Related U.S. Application Data

[62] Division of Ser. No. 979,019, Nov. 20, 1992, Pat. No. 5,300,509.

[30] Foreign Application Priority Data

Nov. 25, 1991 [GB] United Kingdom ............... 9125001

[51] Int. Cl.$^6$ .................. A61K 31/52; C07D 473/34
[52] U.S. Cl. .................. 514/266; 514/261; 514/262; 544/264; 544/265; 544/269
[58] Field of Search .................. 514/261, 262, 514/266; 544/264, 265, 269

[56] References Cited

U.S. PATENT DOCUMENTS 2,807,616  9/1957  Falco et al. ............... 544/255

FOREIGN PATENT DOCUMENTS

| | | |
|---|---|---|
| 0459702 | 12/1991 | European Pat. Off. |
| 02206M | 12/1963 | France . |
| 1190468 | 1/1963 | Germany . |
| 1620498 | 4/1965 | Germany . |
| 1620667 | 12/1965 | Germany . |
| 0035591 | 2/1982 | Japan . |
| 0810699 | 4/1981 | U.S.S.R. . |
| 0988481 | 1/1963 | United Kingdom . |
| 9009178 | 8/1990 | WIPO . |

OTHER PUBLICATIONS

Hassan et al, Carbohydrate Research 34, pp. 203–207, 1974.
H. S. El Khadem and R. Sindric, "Synthesis of a 8–(hydroxyalkyl)adenines*", Carbohydrate Research, May 1974, vol. 34, No. 1, pp. 203–207.
Sato and Saito, "Studies on Pyrazines. 17. [1]. An Efficient Synthesis of Pteridine–6–Carboxylic Acids," J. Heterocyclic Chem., vol. 25, 1988, pp. 1737–1740.
"Furterene," The Merck Index, 11th Ed., published by Merck and Co., Rahway, New Jersey, 1989, p. 675, entry 4224.
Temple et al., "Synthesis of Potential Antimalarial Agents. VII. Azaquinolines. I. The Preparation of Some Pteridines and Pyrido [3,4–b] pyrazines (1)," J. Heterocyclic Chem., vol. 7, Oct. 1970, pp. 1195–1202.

*Primary Examiner*—Yogendra N. Gupta
*Attorney, Agent, or Firm*—Cushman Darby & Cushman

[57] ABSTRACT

Compounds of formula I, and pharmaceutically acceptable salts thereof,

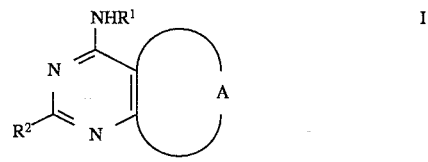

in which $R^1$ is hydrogen (1–6C)alkyl or (1–4C)alkanoyl;

A is —N=CQ—O—, N=CQ—NR$^8$—, —N=CQ—CH=N— or —N=CH—CQ=N—;

Q is 2—furyl;

$R^8$ is hydrogen or C1–4C)alkyl;

and $R^2$ has any of the meanings given in the specification, processes for preparing the compounds and pharmaceutical compositions containing them. The compounds are useful as adenosine antagonists.

9 Claims, No Drawings

FURYL-SUBSTITUTED PURINES AND ADENOSINE ANTAGONISTS

This is a division of application Ser. No. 07/979,019, filed Nov. 20, 1992, now U.S. Pat. No. 5,300,509.

This invention concerns heterocyclic compounds and, more particularly, certain furyl-substituted purines, oxazolopyrimidines and pteridines which have useful pharmacological properties (and in particular antagonise the actions of adenosine such as vasodilation). The invention also includes pharmaceutical compositions containing the heterocyclic compounds for use in treating certain diseases and disorders affecting mammalian cardiac, peripheral and/or cerebral vascular systems. Also included are processes for the manufacture and formulation of the heterocyclic compounds.

The compound theophylline (1,3-dimethylxanthine) has been used clinically (usually as its ethylene diamine salt, which is also known as aminophylline) as a respiratory stimulant, a centrally acting stimulant, a bronchodilator, a cardiac stimulant and as a diuretic. This diversity of clinical uses is an indication of the range of pharmacological actions which have been attributed to theophylline. These include phosphodiesterase inhibition, adenosine receptor antagonism, mobilisation of intracellular calcium and the release of catecholamines. Recently theophylline has also been reported to be useful in treating myocardial ischaemia (Haseri et al., *The Lancet*, 1989, 683–686), skeletal muscle ischaemia (Picano et al., *Angiology*, 1989, in press) and cerebral ischaemia (Skinhoj et al., *Acta. Neurol. Scand.*, 1970, 46, 129–140). The beneficial effects of theophylline in these ischaemic disorders are believed to be due to a reduction or prevention of the phenomenon known as "vascular steal" by virtue of the compound's ability to antagonise the actions of adenosine by blocking the adenosine receptors which mediate metabolism-linked vasodilatation.

The "vascular steal" phenomenon can occur when the major artery supplying a particular vascular bed is partially or totally occluded resulting in ischaemia. In this situation, the compromised vascular bed dilates and blood flow is maintained by either an increase in flow across the narrowed vessel or by an increase in flow through the collateral vessels. However, increased metabolic activity in adjacent vascular beds results in release of mediators such as adenosine, causing them to dilate, resulting in the limited blood flow to the compromised vascular bed being "stolen" by these adjacent areas. The loss of blood from compromised to normally perfused vascular beds by the phenomenon of "vascular steal" further diminishes the blood flow in the compromised vascular bed.

The diversity of pharmacological properties possessed by theophylline make it difficult to use in the regular treatment or prevention of occlusive diseases and conditions of the vasculature. Thus, its associated action as a phosphodiesterase inhibitor results in cardiac stimulation which is deleterious for patients with myocardial ischaemia. Furthermore, the relatively low potency of theophylline means that dose-levels which are therapeutically useful are close to those which can cause serious central side-effects.

Several furyl-substituted purine and pteridine compounds are known. El Khadem, H. S. and Sindric, R., Carbohydrate Research, 34, (1974), 203–207 discloses 6-amino-8-(2-furyl)-1H-purine. This compound was obtained as a byproduct during the synthesis of certain 6-amino-8-hydroxyalkyl-1H-purines. The compound 2,4,7-triamino-6-(2-furyl)pteridine (also called furterene) is known as a diuretic.

We have now discovered (and this is a basis for our invention) that a group of furyl-substituted purines, oxazolopyrimidines and pteridines of formula I defined below are effective antagonists of the actions of adenosine and in particular of its vasodilatory actions.

According to the invention there is provided a compound of the formula I set out hereinafter (together with the other formulae appearing in Roman numerals)wherein: $R^1$ is hydrogen, (1–6C)alkyl, or (1–4C)alkanoyl; $R^2$ is hydrogen, cyano or a group of formula $R^3X$; $R^3$ (when not as hereinbelow defined together with X) is (3–12C)cycloalkyl, (3–6C)alkenyl, phenyl(3–6C)alkenyl, 5- or 6-membered heteroaryl, optionally substituted (1–6C)alkyl or optionally substituted phenyl, said optionally substituted alkyl being unsubstituted or substituted by one of (3–6C)cycloalkyl, optionally substituted 5- or 6-membered heteroaryl, optionally substituted phenyl and a group of formula $R^4(CO)_nX_a(CO)_m$ in which $R^4$ is (1–6C)alkyl, (3–6C)cycloalkyl, optionally substituted phenyl or optionally substituted phenyl(1–4C)alkyl, n and m are each 0 or 1 provided that n+m is 0 or 1, and that when m is 0, X and $X_a$ are separated by at least two carbon atoms, $X_a$ is oxy, thio, sulphinyl, sulphonyl or an imino group of formula -NRb in which Rb is hydrogen, (1–6C)alkyl or together with $R^4$ and the adjacent nitrogen atom forms a 4 to 6-membered saturated heterocyclic ring, said optionally substituted 5- or 6-membered heteroaryl being unsubstituted or substituted by 1 or 2 of (1–4C)alkyl, (1–4C)alkoxy and halogeno, and any of said optionally substituted phenyl being unsubstituted or substituted by (1–4C)alkylenedioxy or by 1,2 or 3 of halogeno, cyano, trifluoromethyl, (1–4C)alkoxycarbonyl, hydroxy, hydroxymethyl, amino, (1–4C)alkanoylamino, (1–4C)alkoxymethyl, (1–4C)alkanoyloxy, benzyloxy, halogenobenzyloxy, (1–4C)alkylsulphonylamino, (1–4C)haloalkylsulphonylamino, nitro, and (1–4C)alkyl or alkoxy optionally bearing a group of formula $R^5CO$ in which $R^5$ is (1–4C)alkoxy, (3–6C)alkylamino, (3–6C)cycloalkylamino or (N-(1–4C)alkyl) (N-(1–4C)dialkylamino(1–4C)alkyl)amino, and sulphamoyl of formula $-SO_2.NR^6R^7$ in which $R^6$ and $R^7$ are independently hydrogen or (1–4C)alkyl, or $R^6$ is hydrogen and $R^7$ is ((2–5C)alkoxycarbonyl)-$(CH_2)q$-, carbamoyl$(CH_2)q$ or (N-(1–4C)alkylcarbamoyl)$(CH_2)q$, in which q is 0 or an integer of from 1 to 4, or $R^6$ is (1–4C)alkyl and $R^7$ is di(1–4C)alkylamino(1–4C)alkyl; and X is a direct bond or oxy, thio, sulphinyl, sulphonyl or an imino group of formula —NRa— in which Ra is hydrogen, (1–6C)alkyl or together with $R^3$ and the adjacent nitrogen atom forms a 4 to 6-membered saturated heterocyclic ring; A is —N=CQ—O—, —N=CQ—$NR^8$—, —N=CQ—CH=N— or —N=CH—CQ=N—; Q is 2-furyl; and $R^8$ is hydrogen or (1–4C)alkyl; provided that when $R^1$ and $R^2$ are hydrogen and A is —N=CQ—$NR^8$—, $R^8$ is not hydrogen; or a pharmaceutically acceptable salt thereof.

It will be appreciated that depending on the nature of the substituents, in containing one or more chiral centres, the formula I compounds may exist in and be isolated in one or more different enantiomeric or racemic forms (or a mixture thereof). It is to be understood that the invention includes any of such forms which possesses the property of antagonising the actions of adenosine, it being well known how to prepare individual enantiomeric forms, for example, by synthesis from appropriate chiral starting materials or by resolution of a racemic form. Similarly, the adenosine antagonist properties of a particular form may be readily evaluated, for example by use of one or more of the standard in vitro or in vivo screening tests detailed hereinbelow.

It will also be appreciated that the first nitrogen atom in the group A, reading from left to right, is attached to the pyrimidine ring para to the group R2.

A particular value for $R^1$ when it is (1–6C)alkyl is, for example, methyl, ethyl, propyl or butyl, and when it is (1–4C)alkanoyl is, for example, formyl, acetyl or propionyl.

An example of a particularly preferred value for $R^1$ is hydrogen.

A particular value for $R^3$ when it is (3–12C)cycloalkyl is, for example, cyclopropyl, cyclobutyl, cyclopentyl, cyclohexyl or norbornyl.

A particular value for $R^3$ when it is (3–6C)alkenyl is allyl.

A particular value for $R^3$ when it is phenyl(3–6C)alkenyl is 3-phenyl-2-trans-propenyl.

Particular values for $R^3$ when it is 5- or 6-membered heteroaryl include, for example, pyridyl, isoxazolyl or thiadiazolyl.

Particular values for an alkyl group when $R^3$ is optionally substituted (1–6C)alkyl are, for example, methyl, ethyl, isopropyl, propyl, butyl, sec-butyl and n-pentyl.

Particular values for optional substituents on alkyl when $R^3$ is optionally substituted alkyl (such as methyl or ethyl) include, for example: for (3–6C)cycloalkyl: cyclopropyl; for optionally substituted 5- or 6-membered heteroaryl:

for the 5- or 6-membered heteroaryl: furyl, pyridyl or thienyl;

for the optional substituents:

for (1–4C)alkyl: methyl;

for (1–4C)alkoxy: methoxy; and for halogeno; fluoro, chloro or bromo;

for a group of formula $R^4(CO)_nXa(CO)_m$:

for $R^4$: methyl, ethyl, n-propyl, cyclohexyl, phenyl or 4-hydroxybenzyl, for $X_a$: oxy, thio, NH, methylimino or, together with $R^4$, piperidino.

It will be appreciated that when $R^3$ represents the group $R^4(CO)mXa(CO)M$, n is 0 when Xa is —NRb, and Rb, together with $R^4$ and the adjacent nitrogen atom form a 4 to 6-membered saturated heterocyclic ring.

Particular values for optional substituents on an optionally substituted 5- or 6-membered heterocyclic ring include, for example: for alkyl: methyl or ethyl; for alkoxy: methoxy or ethoxy; and for halogeno: fluoro, chloro or bromo.

Particular values for optional substituents on an optionally substituted phenyl (for example where $R^3$ is optionally substituted phenyl or optionally substituted phenyl(1–6C)alkyl) include, for example:

for alkylenedioxy: methylenedioxy;

for halogeno: fluoro, chloro or bromo;

cyano;

trifluoromethyl;

for alkoxycarbonyl: methoxycarbonyl;

hydroxy;

hydroxymethyl;

amino;

for (1–4C)alkanoylamino:acetamido for (1–4C)alkoxymethyl: methoxymethyl;

for alkanoyloxy: pivaloyloxy;

benzyloxy;

for halogenobenzyloxy: 4-fluorobenzyloxy or 4-chlorobenzyloxy;

for (1–4C)alkylsulphonylamino: methylsulphonylamino;

for (1–4C)haloalkylsulphonylamino: trifluoromethylsulphonylamino;

nitro;

for (1–4C)alkyl or alkoxy optionally substituted by a group of formula $R^5CO$:

for (1–4C)alkyl: methyl or ethyl;

for (1–4C)alkoxy: methoxy or ethoxy;

for $R^5$:

for (1–4C)alkoxy: methoxy, ethoxy or t-butoxy;

for (3–6C)alkylamino: n-propylamino;

for (3–6C)cycloalkylamino: cyclopentylamino or cyclohexylamino;

for (N-(1–4C)alkyl, N,N-(1–4C)dialkylamino(1–4C)alkylamino: (N-methyl, N,N-dimethylaminoethyl)amino; for sulphamoyl of formula —$SO_2NR^6R^7$: for $R^6$ and $R^7$ are independently hydrogen or (1–4C)alkyl: —$SO_2NH_2$ or —$SO_2N(CH_3)_2$; for $R^6$ is hydrogen and $R^7$ is ((2–5C)alkoxycarbonyl)$(CH_2)_q$-, carbamoyl$(CH_2)_q$- or (N-1–4C)alkylcarbamoyl)$(CH_2)_q$: $R^7$ is methoxycarbonylmethyl, carbamoylmethyl or N-methylcarbamoylmethyl; for $R^6$ is (1–4C)alkyl and $R^7$ is di(1–4C)alkylamino(1–4C)alkyl: $R^6$ is methyl and $R^7$ is dimethylaminoethyl, dimethylaminopropyl or dimethylaminobutyl.

One of the substituents on a substituted phenyl group is preferably in the para position.

A particular value for Ra when it is (1–6C)alkyl is, for example, methyl or ethyl.

Particular values for X include, for example, oxy, thio, NH, methylimino or, together with $R^3$, morpholino, thiomorpholino, pyrrolidino, piperidino or azetidino.

Particular values for $R^8$ include, for example hydrogen and methyl.

A group of compounds of particular interest consists of those compounds of formula I wherein:

$R^1$ is hydrogen;

$R^2$ is $R^3X$ $R^3$ is (1–4C)alkyl, (3–6C)alkenyl, pyridyl(1–4C)alkyl or phenyl(1–4C)alkyl optionally substituted on the phenyl moiety by 1 or 2 of halogen, hydroxy, (1–4C)alkanoyloxy, (1–4C)alkyl and (1–4C)alkoxy;

X is a direct bond, oxy, thio or NH;

A is —N=CQ—O—, —N=CQ—NR$^8$—, —N=CQ—CH=N— or —N=CH—CQ=N—;

Q is 2-furyl; and $R^8$ is hydrogen or methyl;

and pharmaceutically acceptable salts thereof.

Of this group of compounds, those wherein $R^2$ is a 4-chlorobenzyl, 2-phenylethyl, 2-phenylethylamino, 2-(4-hydroxyphenyl)ethylamino, 2-(4-methylphenyl)ethylamino, 2-(4-methoxyphenyl)ethylamino or 2-(3,4-dimethoxyphenyl)ethylamino are especially preferred.

Particular pharmaceutically acceptable salts include, for example, salts with acids affording physiologically acceptable anions, for example, salts with strong acids, such as hydrochloric, hydrobromic, sulphuric, phosphoric, methanesulphonic and trifluoracetic acids. In addition, for those compounds of formula I which are sufficiently basic, suitable salts include, for example, salts with organic acids affording a physiologically acceptable anion such as salts with oxalic, citric or maleic acid. Certain compounds of formula I, for example those in which $R^2$ comprises a phenol group, may form base salts with bases affording physiologically acceptable cations, such as alkali metal and alkaline earth metal salts.

Specific compounds of the formula I which are of interest are described hereinafter in the accompanying examples, and the pharmaceutically acceptable acid-addition salts thereof, and these are provided as a further feature of the invention.

The compounds of formula I may be manufactured using procedures analogous to those well known in the arts of heterocyclic and organic chemistry for the production of structurally analogous compounds. Such procedures are included as a further feature of the invention and include the following preferred procedures for the manufacture of a compound of the formula I in which $R^1$, $R^2$, X, A and Q have any of the meanings defined above:

(a) A compound of formula II in which $Z^1$ is a suitable leaving group, for example halogeuo (such as chloro or bromo) is reacted with a compound of formula $R^1NH_2$.

The process is conveniently effected at a temperature in the range of, for example, from 0° to 120° C. Suitable solvents for the process include alcohols such as ethanol or isopropanol, and ethers such as tetrahydrofuran. When $R^1$ is hydrogen, it is particularly convenient to employ a solution of ammonia in an alcohol, such as ethanol or isopropanol, at ambient temperature.

(b) Reacting a compound of formula III or a salt thereof with a compound of formula IV or a salt thereof, in which either $R^9$ is a leaving group (such as (1–4C) alkoxy, for example ethoxy) and $X^1$ is O or NH, or $R^9$ is CHO and $X^1$ is NH, and $X^2$ is O, S or NH.

The reaction may conveniently be performed in the presence of a solvent such as an alcohol (for example ethanol), a tertiary amine (for example pyridine) or a halogenated hydrocarbon, (for example chloroform). Preferably it is performed in the presence of a base, such as a tertiary amine (for example dimethylaminopyridine or pyridine). The temperature at which the reaction is performed is conveniently in the range of from 25° to 150° C., for example from 60° to 100° C.

When using fural-2-glyoxal as the compound of formula IV to prepare a glyoupond of formula I in which A is —N═CH—CQ═N— or —N═CQ—CH═N—, the solvent conveniently comprises ethanol and water.

When a compound of formula I in which A is —N═CQ—CH═N— is desired, the reaction is preferably performed in the presence of an acid, for example a mineral acid such as sulphuric acid or hydrochloric acid.

(c) For the preparation of a compound of Formula I which A is —N═CQ—O— or —N═CQ—NR$^8$— cyclising a compound of formula V in which one of $R^{10}$ and $R^{11}$ is hydrogen and the other is a group of formula $C(=X^4)Q$ in which $X^3$ is O or NH, and $X^4$ is O, S or NH.

The compound of formula V may conveniently be cyclised by treatment with a dehydrating agent, for example phosphorus pentoxide or phosphorus oxychloride. The cyclisation may be performed in the presence or absence of a solvent, conveniently at a temperature in the range of from 0° to 150° C., for example from 50° to 120° C.

(d) For the preparation of a compound of formula I in which A is —N═CQ—NR$^8$— and $R^8$ is (1–4C)alkyl, reacting a corresponding compound of formula I in which $R^8$ is hydrogen with an appropriate alkylating agent.

The alkylating agent may be a conventional alkylating agent such as a (1–4C)alkyl halide or di(1–4C)alkyl sulphate. The reaction is conveniently performed in the presence of a base, such as an alkali metal carbonate or hydroxide (for example, potassium carbonate). Suitable solvents for the reaction include amides (for example dimethylformamide), ethers (for example tetrahydrofuran) and alcohols (for example ethanol). The temperature at which the reaction is performed is conveniently in the range of from 0° to 100° C.

(e) Reacting a compound of formula VI with an amidine of formula VII or, for a compound where $R^2$ is cyano, a cyanogen halide and an alkali metal cyanide.

The reaction may conveniently be performed in the presence of a solvent such as an amide (for example dimethylformamide), and at at temperature in the range of from 25° to 150° C., for example from 60° to 120° C. The reaction may conveniently be performed in the presence of a strong base, for example an alkali metal alkoxide such as potassium t-butoxide.

(f) For a compound of formula I in which X is O, S or $NR_a$, reacting a compound of formula VIII in which $Z^2$ is a leaving group such as a (1–4C)alkylsulphonyl group (for example methylsulphonyl) with a compound of formula $R^3XH$ or a salt thereof.

The reaction may conveniently be performed in the presence of a solvent such as a nitrile (for example acetonitrile), an ether (for example t-butyl methyl ether, tetrahydrofuran or 1,2-dimethoxyethane) or an amide (for example dimethylformamide), and at a temperature in the range of from 10° to 120° C., for example from 30° to 80° C. The reaction is preferably performed under basic conditions, which may be provided by the inherent basicity of the compound of formula R3XH or a salt thereof, or by a base such as a tertiary amine, for example pyridine or triethylamine, or an alkali metal alkoxide, for example sodium ethoxide.

It will be appreciated that those compounds in which $R^1$ is other than hydrogen may also be obtained by carrying out a conventional alkylation or acylation of the corresponding formula I compound in which $R^1$ is hydrogen obtained by one of processes (a)–(f) above.

It will also be appreciated that those compounds of formula I in which $R^3$ contains an acyloxy group, for example where $R^3$ is (1–4C)alkanoyloxyphenyl or (1–4C)alkanoyloxyphenyl(1–6C)alkyl, may be prepared by acylating the corresponding compounds of formula I in which $R^3$ comprises a hydroxy group, as for example where $R^3$ is hydroxyphenyl or hydroxyphenyl(1–4C)alkyl. The acylation may be conducted by reaction with any conventional acylating agent, for example a (1–4C)alkanoyl halide or (1–4C)alkanoic acid anhydride.

Whereafter, when a pharmaceutically acceptable salt is required, it may be obtained, for example, by reacting a compound of formula I with the appropriate acid or base affording a physiologically acceptable ion or another conventional procedure.

Similarly, when an optically active form of a chiral compound of formula I is required, either one of processes (a)–(f) above may be carried out using the appropriate optically active starting material or else a racemic form may be resolved by a conventional procedure, for example, using an optically active form of a suitable acid.

The starting materials used in the processes according to the invention are either known or may be prepared using techniques well known in the arts of heterocyclic and organic chemistry.

Thus the compounds of formula II in which $Z^1$ represents a halogen atom may be prepared from a compound of formula IX in which $R^{12}$ represents a hydrogen atom or an alkoxy group (for example ethyl) and $R^{13}$ and $R^{14}$ are as defined for $R^{10}$ and $R^{11}$ above according to the method of process (c) above, but using as the dehydrating agent a reagent which is also a halogenating agent, for example phosphorus oxychloride. The reaction may be performed in the presence or absence of a solvent (such as dimethylformamide) at a temperature in the range of from 0° to 150° C.

The compounds of formula III may be prepared by reacting a compound of formula X with a reducing agent, for example sodium dithionite, conveniently in the presence of a solvent such as aqueous ethanol. Compounds of formula III in which $R^2$ represents a group capable of functioning as a leaving group, for example a (1–4C)alkylthio group (such as methylthio) may also be converted into other compounds of formula III by reaction with a nucleophilic compound of formula $R^3XH$ where X is, for example, NH. The reaction may conveniently be performed in the presence of a solvent such as water at a temperature in the range of from 40° to 120° C.

The compounds of formula V in which one of $R^{10}$ and $R^{11}$ is a group of formula $C(=X^4)Q$ may be prepared by reacting a compound of formula III with a compound of formula IV in which $R^9$ is a leaving group such as a halogen atom (for example a chlorine atom). The reaction is conveniently performed in the presence of a solvent such as chloroform and in the presence of a base such as triethylamine. The temperature at which the reaction is performed is conveniently in the range of from 0° to 100° C. Compounds of formula V in which $R^2$ represents a group capable of functioning as a leaving group, for example a (1–4C)alkylthio group (such as methylthio) may also be converted into other compounds of formula V by reaction with a nucleophilic compound of formula $R^3XH$ where X is, for example, NH. The reaction may conveniently be performed in the presence of a solvent such as water at a temperature in the range of from 40° to 120° C.

The compounds of formula VI may be prepared by conventional methods. For example, the compounds of formula VI in which A is —N=CQ—CH=N— may be prepared according to the method described in J. Het. Chem., 25, 1737–1740, 1988.

The compounds of formula VIII may be prepared by methods analagous to those which may be used to prepare compounds of formula I. Compounds of formula VIII in which $Z^2$ represents a (1–4C)alkylsulphonyl group may be prepared by reacting a compound of formula I in which $R^2$ represents a (1–4C)alkylthio group with an oxidising agent such as peracetic, perbenzoic or chloroperbenzoic acid. The oxidation may conveniently be performed in the presence of a solvent such as dichloromethane at a temperature in the range of 0° to 40° C.

The compounds of formula IX may be prepared by reacting a compound of formula VII with a compound of formula $(R^{15}OOC)CHNHCOQ$ in which $R^{15}$ is a (1–4C)alkyl group such as ethyl, or with a compound of formula XII (preparable by reacting a compound of formula $(R^{15}OOC)CHNHCOQ$ with a dehydrating agent such as phosphorus pentoxide supported on silicon dioxide). The reaction is conveniently performed in the presence of a base, such as sodium methoxide or potassium carbonate, and a solvent such as dimethylformamide. The temperature at which the reaction is performed is conveniently in the range of from 25° to 120° C.

The compounds of formula X may be prepared by reacting a compound of formula XI with an alkali metal nitrite in the presence of an acid such as hydrochloric acid. The reaction is conveniently performed in the presence of a solvent such as aqueous ethanol at a temperature in the range of from 25° to 100° C. The compounds of formula X may also be prepared by reacting a compound of formula VII with an appropriate oxime. For example, a compound in which X is 0 may be prepared using NCC(COOEt)=NOH as the oxime.

Certain of the starting materials used in the processes according to the invention are believed to be novel, for example the compounds of formulae II and VIII, and these are provided as further aspects of the invention.

As stated above, the compounds of formula I possess the property of antagonising one or more of the physiological actions of adenosine and are valuable in the treatment of diseases and medical conditions affecting the mammalian cardiac, peripheral and/or cerebral vascular systems, such as ischaemic heart disease, peripheral vascular disease (claudication) and cerebral ischaemia. The compounds may also be useful in the treatment of migraine.

The effects of compounds of formula I as adenosine receptor antagonists may be demonstrated in one or more of the following standard in vitro and/or in vivo tests.

(a) $A_2$ Adenosine receptor affinity test

This test involves the ability of a test adenosine antagonist to displace the known adenosine mimetic agent [$^3$H]-N-ethylcarboxamidoadenosine (NECA) from binding sites on membrane preparations derived from the rat phaeochromocytoma cell line PC 12 (available from the Beatson Institute, Glasgow). The basic procedure has been described by Williams et al. (J. Neurochemistry, 1987, 48(2), 498–502).

The membrane preparation is obtained as follows: Frozen pellets of PC12 cells are washed twice with ice cold, buffered, physiological saline and the cells recovered by centrifugation (1500 G) at 3° C. The separated cells are then suspended in hypotonic solution (distilled water), allowed to stand on ice for 30 minutes and are then carefully homogenized using a standard high-speed homogeniser with periodic ice-cooling to obtain a fine suspension. The homogenate is centrifuged (48000 G) and the pellet is resuspended in 50 mM tris-HCl buffer, pH 7.4 containing adenosine deaminase (5 units/ml, Type VII from calf intestinal mucosa, available from Sigma Chemical Corporation, under reference no. A1280). The mixture is then incubated at 37° C. After 20 minutes, the reaction is terminated by dilution with ice-cold buffer and transfer onto ice. The material obtained containing the cell membranes is recovered by centrifugation and washed by resuspension in buffer and recentrifugation. The pellet produced is then resuspended in ice-cold buffer using a hand-driven homogenizer. The resultant membrane suspension is frozen and stored under liquid nitrogen until required.

Binding studies are carried out in microtitre plates, the assay mixtures being buffered in 50 mM tris-HCl, pH 7.4 at room temperature. The test compound is dissolved in dimethyl sulphoxide (DMSO) and then diluted with assay buffer to give the test solutions. [The final concentration of DMSO is not allowed to exceed 1% by volume, at which level it does not affect radioligand binding to the membrane receptor.] Incubations are performed at 30° C. for 90 minutes in a total volume of 150 µl comprising the test solution or buffer (50 µl), tritiated NECA (50 µl) and membrane suspension (50 µl). After incubation, the samples are rapidly filtered over glass-fibre mats and the filter mats are washed to remove non-receptor-bound radioligand. Receptor-bound radioligand entrapped on the filter mats is then determined by liquid scintillation counting. Filtration and washing are carried out using a conventional vacuum filtration cell harvester. The specific binding (defined as the difference between the total binding and the non-specific binding) in the presence of the particular test compound is determined and compared with the control value. Results are conveniently expressed as the negative logarithm of the concentration required to cause a 50% displacement of control specific binding ($pIC_{50}$).

In general, compounds of the formula I showing antagonist activity in this assay typically show a $pIC_{50}$ in the above test (a) of 6 or more. Thus for example, the compound of Example 1 herein showed a 78% displacement of control binding at a concentration of $10^{-5}$M and 59% displacement at $10^{-7}$M, indicating a $pIC_{50}$ of greater than 7. Using the same test procedure, the known compound 1,3-dimethylxanthine typically shows a $pIC_{50}$ of about 5.

(b) Guinea-pig Atrial Bradycardic Test

This test has also been described by Collis et al. (*British J. Pharmacolog*, 1989, 97, 1274–1278) and involves the ability of a test compound to antagonise the bradycardic effect of the adenosine mimetic, 2-chloroadenosine, in a beating guinea-pig atrial preparation, an effect mediated via the adenosine receptor known as $A_1$.

The atrial pair preparation may be obtained as follows: Atrial pairs are obtained from guinea-pigs (Dunkin Hartley strain, 250–400 g males) and mounted in organ baths containing oxygenated Krebs buffer solution (95% $O_2$; 5% $CO_2$) at 37° C. The spontaneously beating atria are then placed under a resting tension of 1 g and allowed to equilibrate for 50 minutes with continuous overflow. Overflow is then stopped and adenosine deaminase (1 Unit\ml) added to prevent the accumulation of endogenously produced adenosine. After equilibration for 15 minutes, a cumulative dose response curve to the adenosine mimetic, 2-chloroadenosine ($10^{-8}$M to $10^{-4}$M) is administered to produce a maximal slowing of atrial rate. After washout during 30 minutes, adenosine deaminase is readministered to the bath which is allowed to equilibrate for 15 minutes. A $10^{-5}$M solution of the test compound in DMSO is then added to the bath which is left to incubate for 30 minutes. Any effect on the beating rate due to the test compound is noted before the dose response curve to 2-chloroadenosine is repeated. Compounds which are adenosine antagonists attenuate the 2-chloroadenosine response.

Test compounds are assessed by comparing dose response curves to 2-chloroadenosine alone with those obtained in the presence of the compound. Competitive adenosine antagonists produce a parallel shift in the 2-chloroadenosine dose response curve. The dose ratio (DR) is calculated from the ratio of the concentration of 2-chloroadenosine to produce a 50% reduction in atrial rate ($ED_{50}$) in the presence of the test compound divided by the $ED_{50}$ concentration of 2-chloroadenosine in the absence of the test compound for each atrial pair. The pA2, which is an estimate of the concentration of antagonist required to give a dose ratio of 2, may be calculated using a standard computational technique. In this test, the known compound, 1,3-dimethylxanthine, typically shows a pA2 of about 5.

(c) Anaesthetised cat blood pressure Test

This test assesses the ability of a test compound to antagonise the fall in diastolic blood pressure produced by administration of the adenosine mimetic, 2-chloroadenosine.

Male cats (2–3 kg) are anaesthetised with sodium pentobarbitone (45 mg/kg, ip). The following blood vessels are catheterised: right jugular vein (for infusion of the anaesthetic at approximately 7 mg/kg per hour as a 3 mg/ml solution in isotonic saline), the left jugular vein (for administration of test agents) and the right common carotid artery (for monitoring blood pressure and pulse rate). The blood gas status and pH are determined, and are maintained within physiological limits, before administration of 2-chloroadenosine. A control dose response curve (DRC) to 2-chloroadenosine (0.3 to 30 µg/kg) against the fall in diastolic blood pressure is determined. A solution of the test compound in a mixture of 50% v/v polyethylene glycol (PEG) 400 and 0.1M sodium hydroxide is then administered i.v. and after 15 minutes the DRC to 2-chloroadenosine is determined. This procedure is repeated twice with blood gases and pH being monitored and maintained within physiological limits between each DRC. The concentration of 2-chloroadenosine required to cause a 30 mm Hg fall in diastolic blood pressure is then calculated for each dose of test compound and a Schild plot constructed for those which produce a dose ratio (DR) of >2. From this plot a $K_B$ value is determined. Test compounds which are active in this test will possess a $K_B$ value of 1 mg/kg (or much less).

The above Test (c) may conveniently be modified to allow evaluation of orally administered test compounds by administering the test compound to conscious cats with indwelling arterial and venous catheters and measuring the effect in preventing an adenosine induced decrease in blood pressure. Test compounds which are orally active in this test will show significant adenosine antagonist activity at a dose of 1 –3 mg/kg or less.

(d) Anaesthetised dog Test

This test involves the assessment of the effects of a test compound on antagonising the actions of adenosine in lowering heart rate and producing vasodilation (as measured by a fall in hind-limb perfusion pressure).

Beagles (12 –18 kg) are anaesthetised with sodium pentobarbitone (50 mg/kg, iv). The following blood vessels are catheterised: right jugular vein (for infusion of the anaesthetic at approximately 112 mg per hour as a 3 mg/ml solution in isotonic saline), right brachial vein (for administration of drugs and test agents), right brachial artery (for measurement of systemic blood pressure and pulse rate) and the left carotid artery (for administration of adenosine into the left ventricle). Both vagi, the right femoral and sciatic nerves are ligated and severed. A bolus injection of 1250 U heparin is administered before perfusing the right hindlimb at constant blood flow with blood from the iliac artery. The right leg is tied Just below the ankle. Xamoterol (1 mg/kg) is then administered to the animal to stabilise heart rate at a high level and nitrobenzylthiotnosine (NBTI, 0.5 mg/kg) to inhibit the uptake of adenosine. The animal is sensitised to adenosine during the equilibration time following NBTI by carrying out a dose response curve (DRC). During this time any blood gas or pH imbalance is corrected. A control DRC is performed followed by up to three DRC's after cumulative administration of the test compound (as described in (d) above). Each DRC is carried out 15 minutes after administration of test compound and after the measured parameters of heart rate and hindlimb perfusion pressure have returned to a stable state. Similarly, blood gases and pH are maintained within physiological limits throughout the evaluation.

The amount of adenosine required to cause a 50% fall in measured parameter ($ED_{50}$) i.e. heart rate and hindlimb perfusion pressure is calculated for each does of test compound and a Schild plot constructed. From this plot a $K_B$ value is determined for antagonism of heart rate response and vasodilator response to adenosine. Test compounds which are active in this test will possess a $K_B$ value of 1 mg/kg (or much less) for vasodilator response to adenosine.

(e) Anaesthetised cat exercise hyperaemia test

This test involves assessment of the effect of a test compound to antagonise the vasodilatation response which occurs during twitch contraction of skeletal muscle. The vasodilation is mediated partly by the release of endogenous adenosine from the contracting skeletal muscle.

Cats (2.4–3.6 kg) are anaesthetised with sodium pentobarbitone (50 mg.kg$^{-1}$ip). The following blood vessels are catheterized: left jugular vein (for infusion of anaesthetic, at approximately 0.12 mg$^{-1}$min$^{-1}$ as a 6 mg.ml$^{-1}$ solution in isotonic saline), right external Jugular vein (for administration of drugs and test compounds), right common carotid artery (for measurement of systemic arterial blood pressure and pulse rate) and right brachial artery (for withdrawal of blood).

Blood flow to the left hind limb is measured with an electromagnetic flow probe around the left external iliac artery. The whole of the left hind limb is made to contract at 3 Hz for 20 minutes duration by stimulating the sciatic and femoral nerves. Active tension produced by the extensor digitorum longus and peroneous longus muscles is measured isometrically with a force transducer. Exercise is repeated twice within the same animal, in either the absence or presence of the test compound. Test compounds are assessed for their ability to reduce the vasodilatation during skeletal muscle contraction. Test compounds which are active in this test will show significant inhibition of vasodilation during exercise at a dose of 1 mg/kg (or much less).

The compounds of the invention are generally best administered to warm-blooded animals for therapeutic or prophylactic purposes in the treatment or prevention of cardiovascular diseases and adverse conditions in the form of a pharmaceutical composition comprising a compound of formula I or a pharmaceutically acceptable salt thereof, in a mixture or together with a pharmaceutically acceptable diluent or carrier. Such compositions are provided as a further feature of the invention.

In general, it is envisaged that a compound of formula I will be administered orally, intravenously or by some other medically acceptable route (such as by inhalation, insufflation, sub-lingual or transdermal means) so that a dose in the general range, for example, 0,001 mg to 10 (and more particularly in the range, for example, 0.05 to 5 mg/kg) mg/kg body weight is received. However, it will be understood that the precise dose administered will necessarily vary according to the nature and severity of the disease or condition being treated and on the age and sex of the patient.

A composition according to the invention may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose from containing, for example, 5–200 mg of the compound of formula I or an equivalent amount of a pharmaceutically acceptable salt thereof.

The compositions may be obtained by conventional procedures using pharmaceutically acceptable diluents and carriers well known in the art. Tablets and capsules for oral administration may conveniently be formed with an enteric coating (such as one based on cellulose acetate phthalate) to minimise the contact of the active ingredient of formula I with stomach acids.

The compositions of the invention may also contain one or more agents known to be of value in the diseases or conditions of the cardiovasculature intended to be treated. Thus, they may contain, in addition to the compound of formula I, for example: a known platelet aggregation inhibitor, prostanoid constrictor antagonist or synthase inhibitor (thromboxane $A_2$ antagonist or synthase inhibitor), cyclooxygenase inhibitor, hypolipidemic agent, anti-hypertensive agent, inotropic agent, beta-adrenergic blocker, thrombolytic agent or a vasodilator.

In addition to their use in therapeutic medicine, the compounds of formula I are also useful as pharmacological tools in the development and standardisation of test systems for the evaluation of new cardiovascular agents in laboratory animals such as cats, dogs, rabbits, monkeys, rats and mice.

The invention will now be illustrated by the following non-limiting Examples in which, unless otherwise stated:-

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet; q,quartet; and (vi) all end-products were characterised by microanalysis, NMR and/or mass spectroscopy.

EXAMPLE 1

7-chloro-2-(2-furyl)-5-[2-(4-methoxyphenyl)ethyl] amino-oxazolo[5,4-d]pyrimidine (0.5 g) and ammonium chloride (0.1 g) were added to a saturated solution of ammonia in ethanol (20 ml) and sealed in a Caries tube. The sealed tube was then heated at 100° C. for 18 hours. The cooled reaction mixture was poured into water (200 ml) and the resultant precipitate removed by filtration. The solid was recrystallised from methanol to afford 7-amino-2-(2-furyl)-5-[2-(4-methoxyphenyl)ethyl]asino-oxazolo[5,4-d]pyrimidine (0.23 g, 48.6%), m.p. 194°–196° C.; microanalysis, found: C, 61.5; H, 4.8; N, 19.5%; $C_{18}H_{17}N_5O_3$ requires: C, 61.5; H, 4.9; N, 19.9%; NMR (DMSO-d$^6$); 2.76 (t,2H ArC H$_2$), 3.44(brq 2H, CH$_2$NH), 3.72(s,3H,OMe), 6.70(m,1H furyl-H), 6.28(brs, 1H NH), 6.84(d, 2H, ArH), 7.13 (complex, 5H ArH, NH$_2$furyl-H), 7.89(m,1H, furyl-H); m/e [M+H]$^+$ 352.

The required starting material was prepared as follows:-

1) [(2-furanylcarbonyl)amino]propanedioic acid, diethyl ester (123 g, 457 mM) was added to a stirred mixture of 2-methyl-2-thio-pseudourea sulphate (63.8 g, 229 mM) and sodium methoxide (25% w/w) (105 ml), in methanol (500 ml).

The mixture was stirred at ambient temperature for 15 hrs, then heated under reflux for 24 hours. Further sodium methoxide solution (260 ml) was added and the mixture refluxed for a further 24 hours, cooled, poured into water and acidified with concentrated hydrochloric acid to PH<3. The mixture was then cooled to 0° C. for 4 hours and the resultant precipitate separated by filtration. The solid was washed with methylene chloride, then acetone, and air-dried. Further purification was achieved by suspension in hot water for 0.5 hours. The solid was filtered off and dried at 70° C. for 15 hours in a vacuum oven. This gave 4,6-dihydroxy-5-(2-furanylcarbonyl)amino-2-methylthiopyrimidine (22.5 g) as a white solid (yield 18.5%) m.p. 124°–125° C. NMR: NaOD; 2.66(s,3H, SMe), 4.04(s,1H, NH), 6.83(m, 1H, furyl-H), 7.39(d,1H, furyl-H), 7.88(m,1H, furyl-H); m/e [M+NH$_4$]$^+$ 285:

2) A mixture of 4,6-dihydroxy-5-(2-furanylcarbonyl)amino-2-methylthiopyrimidine (2 g, 7.5 mM), p-methoxyphenethylamine (3.4 g, 22.5 mH), and water (25 ml) was heated at 90° C. for 15 hours. The mixture was then poured into water (100 ml) and acidified with concentrated hydrochloric acid until PH<3. The resultant precipitate was removed by filtration and recrystallised from methanol/water (3:1) to afford 4,6-dihydroxy-5-(2-furanylcarbonyl)amino-2-[(4-methoxyphenyl)ethyl]aminopyrimidine as a white solid (0.46 g, 16.6% yield) m.p >250° C.; NMR: DMSO-d$^6$: 2.75(t, 2H,ArCH$_2$), 3.47(brq,2H,CH$_2$NH), 3.73 (s,3H, OMe), 6.50(brs, 1H, NH), 6.61(m, 1H,furyl-H), 6.87(d,2H,ArH), 7.16(d,2H,ArH), 7.17(s,1H furyl-H), 7.82(d,1H, furyl- H), 8.64(brs,1H,NHCO), 10.58(brs,2H,OH×2); m/e [M+H]$^+$ , 371:

3) A mixture of 4,6-dihydroxy-5-(2-furanylcarbonyl)amino-2-[(4-methoxyphenyl)ethyl]aminopyrimidine (408 mg) and phosphorus oxychloride (5 ml) was heated at 90° C. for 3 hours. The excess phosphorus oxychloride was removed by evaporation, in vacuo, and then by azeotroping with toluene (2×50 ml). The residue was added to water and the resultant precipitate filtered off, washed with water and dried. There was thus produced 7-chloro-2-(2-furyl)-5-[2-(4-methoxyphenyl)ethyl]amino oxazolo[5,4-d]pyrimidine (340 mg, 83.2% yield); m.p.169.5°–171° C.: NMR:DMSO-d$^6$: 2.80(t,2H,ArCH$_2$), 3.48(q,2H, CH$_2$NH), 3.72(s, 3H, OMe), 6.80(m, 1H, furyl-H), 6.85(d,2H,ArH), 7.16(d, 2H,ArH), 7.44(d,1H,furyl-H), 8.07(m, 1H, furyl-H), 8.13(brs,1H,NH).

EXAMPLE 2

7-Amino-5-[2-(3,4-dimethoxyphenyl)ethyl]amino-2-(2-furyl)-oxazolo[5,4-d]pyrimidine was prepared using a procedure similar to that described in Example 1, as a white solid (recrystallised from methanol/hexane); m.p. 155°–158° C.; microanalysis, found: C.59.4; N, 5.0; N, 18.4%; C$_{19}$H$_{19}$N$_5$O$_4$ requires: C, 59.8; H,5.0; N, 18.4%; NMR (DHSO-d$^6$); 2.77(t, 2H, ArCH$_2$), 3.45(q, 2H, CH$_2$NH), 3.72(s, 3H, OMe), 3.75(s,3H, OMe), 6.70(complex, 5H, NH, 3×ArH, furyl-H), 7.14(d, 1H, furyl-H), 7.18(brs, 2H, NH$_2$), 7.92(m, 1H, furyl-H); m/e, [M+H]$^+$, 382:

The required starting materials were prepared as in Example 1. This gave 4,6-dihydroxy-2-[(3,4-dimethoxyphenyl)ethyl]-amino-5-(2-furanylcarbonyl)pyrimidine (45.6% yield) m.p. >250° C.: NHR: DMSO-d$^6$: 2.76(t, 2H, ArCH$_2$), 3.49(q, 2H, NHCH$_2$), 3.72(s, 3H, OMe), 3.75(s, 3H, O Me), 6.47(brs, 1H, NHCH$_2$), 6.61(m, 1H, furyl-H), 6.76(d, 1H,Ar-H), 6.86(m,2H, Ar-H) 7.17(d,1H, furyl-H), 7.82 (brs, 1H, furyl-H), 8.64(s,1H, NHCO), 10. 62(brs, 2H, 2×OH); m/e, [M+H]$^+$ , 401:

7-chloro-5-[(3,4-dimethoxyphenyl)ethyl]amino-2-(2-furyl)-oxazolo[5,4-d]pyrimidine (78% yield) m.p. 176°–177° C.: NMR; DMSO-d$^6$); 2.80(t,2H, ArCH$_2$), 3.51(q, 2H, CH$_2$NH), 3.71(s, 3H, OMe), 3.74(s, 3H, OMe), 6.78(complex, 4H, 3×ArH, furyl-H), 7.43(d,1H, furyl-H), 8.06(m, 1H, furyl-H), 8.13(brs, 1H, NH) m/e [M+H]$^+$ 401.

EXAMPLE 3

7-amino-5-(4-chlorobenzyl)-2-(2-furyl)-oxazolo[5,4-d]-pyrimidine was prepared in a manner similar to that described in Example 1 except that no sealed tube was required and the reaction was carried out at ambient temperature using ammonia in isopropanol for 15 hours. The product was purified using flash column chromatography, eluting with methanol/chlorofonn (5/95). There was thus obtained a white solid m.p. >200° C.; microanalysis, found; C, 58.8; H, 3.7%; C$_{16}$H$_{11}$N$_4$O$_2$Cl requires: C, 58.8; H, 3.4%; NMR; DMSO-d$^6$; 4.00(s, 2H, ArCH$_2$), 6.79(m, 1H, furyl-H), 7.32(d, 1H, furyl-H), 7.33(s, 4H, ArH), 7.75(brs, 2H, NH$_2$), 8.03 (d, 1H, furyl-H).

The starting material was prepared as follows:-

1) A mixture of [(2-furanylcarbonyl)amino]propanedioic acid, diethyl ester (53 g, 0.2M) and acetonitrile (1 litre) was stirred at ambient temperature. Phosphorus pentoxide supported on silicon dioxide (90 g) was then added slowly with brisk stirring. The mixture was heated to reflux for 2 hours and then allowed to cool over 15 hours. A further portion of phosporus pentoxide supported on silicon dioxide (85 g) was added, the mixture refluxed for seven hours and then cooled over 15 hours. The mixture was filtered through diatomaceous earth and the filtrate evaporated under reduced pressure to give a yellow gum. More of this product was obtained by extraction of the filter solids with ethyl acetate, followed by evaporation of the solvent under reduced pressure.

The gum was purified by flash column chromatography, eluting with ethyl acetate/hexane (1:4). The resultant solid was recrystallised from methanol/water to give 4-carboxyethyl-5-ethoxy-2-(2-furyl)-oxazole as a solid (12.5 g, 25% yield); NMR: 1.28(t, 3H, CH$_3$CH$_2$O) 1.40(t, 3H, CH$_3$CH$_2$OOC), 4.25(q, 2H, CH$_3$CH$_2$O), 4.57(q, 2H, CH$_3$CH$_2$OOC), 6.71(m, 1H, furyl-H), 7.12(d, 1H, furyl-H), 7.92(d, 1H, furyl-H).

2) A mixture of 5-carboxyethyl-4-ethoxy-2-(2-furyl)-oxazole (4.0g, 0.016M), p-chlorobenzylamidine hydrochloride (3.7 g, 0.016M), anhydrous potassium carbonate (4.4 g, 0.032M) and dry dimethylformamide (80 ml) was heated at 100° C. under argon for 3 hours. The solvent was then distilled off under reduced pressure and the residue partitioned between ethyl acetate and water. The ethyl acetate layer was separated, dried, and concentrated to give an oil. This was purified by flash column chromatography eluting with methanol/chloroform (1:9). There was thus obtained 2-p-chlorobenzyl-4-ethoxy-5-(2-furanylcarbonyl)amino-6-hydroxypyrimidine as a pink/white solid (2.2 g, 35% yield) m.p. 91.5°–92.5° C.; NMR; 1.20(t, 3H, CH$_3$CH$_2$O), 3.91(s, 2H, ArCH$_2$), 4.28(q,2H, CH$_3$CH$_2$O) 6.65(m,1H, furyl-H), 7.71(d, 1H, furyl H), 7.42(s, 4H, ArH), 7.86(m, 1H, furyl-H), 9.02 (s, 1H, NHCO), 12.70(brs, 1H, OH).

3. A mixture of 2-p-chlorobenzyl-4-ethoxy-5-(2-furanylcarbonyl)amino-6-hydroxypyrimidine (2.2 g, 5.9 mM), dimethylaniline (1.12 ml, 9 mM) and phosphorus oxychloride (20 ml) was heated at reflux for 2 hours. The excess phosphorous oxychloride was distilled off under reduced pressure and the residue azeotroped (x 2) with toluene. The residue was partitioned between ethyl acetate and water. The ethyl acetate extracts were dried and the solvent removed under reduced pressure. The resultant solid was further purified by flash column chromatography, eluting with hexane/ethyl acetate (65:35). There was thus obtained 7-chloro-5-(4-chlorobenzyl)-2-(2-furyl)- -oxazolo[5,4-d]pyrimidine (1.2 g), which was used directly without being characterised.

EXAMPLE 4

A mixture of 6-amino-8-(2-furyl)-2-[2-(4-methoxy-phenyl)ethyl]amino-1H-purine (0.8 g, 2.29 mM), anhydrous potassium carbonate (0.347 g, 2.52 mM), iodomethane (157 μl, 2.52 mM) and dimethyl formamide (20 ml) was stirred at ambient temperature under an argon atmosphere for 15 hours. The solvent was removed by distillation under reduced pressure and the residue purified by flash column chromatography eluting with methanol/methylene chloride (1:20). A solid was obtained, and this was triturated with diethyl ether to afford 6-amino-8-(2-furyl)-2-[2-(4-methory-phenyl-ethyl]amino-9-methyl-1H-purine (0.28 g) as a solid; m.p. 147°–149° C.; microanalysis, found: C,62.5; H, 5.3; N, 23.2%; $C_{19}H_{20}N_6O_2$ requires; C, 62.6; H, 5.5; N, 23.1%; NMR: DNSO-$d^6$; 2.7–2.85 (t, 2H, C$H_2$-C$H_2$), 3.35–3.55(q, 2H,C$H_2$N), 3.7–3.8(2s, 6H, OC$H_3$, N-C$H_3$), 6.2–6.35(t,1H, CH$_2$N$H$), 6.7(m,1H,furan-$H$), 6.7–6.8(b,2H, N$H_2$), 6.8–6.9(d,2H, aromatic $H$), 7.0(d,1H, furan-$H$), 7.1–7.25(d, 2H, aromatic-$H$), 7.85(d,1H, furan-$H$).

EXAMPLE 5

A mixture of 2-[2-(4-methoxyphenyl)ethyl]amino-4,5,6-triaminopyrimidine (4.0 g, 14.6 mM), 2-(1-ethoxy-1-imino)methylfuran hydrochloride (3.84 g, 21.9 mM), dimethylaminopyridine (1.78 g, 14.6 mM) and dry pyridine (100 ml) was heated at reflux, under an argon atmosphere, for two hours. The solvent was then removed by evaporation under reduced pressure and the residue purified by flash column chromatography, eluting with methanol/methylene chloride (1:25). There was thus obtained 6-amino-8-(2-furyl)-2-[2-(4-methoxyphenyl)ethyl]amino-1H-purine as a solid (2.42 g, 50% yield) m.p 220°–222° C.; NMR: DMSO-$d^6$; 2.7–2.9(t,2H, C$H_2$—C$H_2$), 3.35–3.55(m,2H, C$H_2$NH), 3.7(s,3H, OC$H_3$), 6.1–6.2(t, 1H, NH), 6.6–6.75(m,3H, N$H_2$+furan 1H), 6.68–6.9(m,2H, aromatic-$H$), 7.0(d,1H, furan-$H$), 7.1–7.2(m,2H, aromatic-$H$), 7.8(s, 1H, furan-$H$), 12.55–12.75(b,1H, N$H$).

The starting material was prepared as follows:- 1) A mixture of 4,6-diamino-2-methylthio-5-nitrosopyrimidine (10 g, 5.4 mM), 4-methoxyphenethylamine (7.92 ml, 5.4 mM) and water (180 ml) was heated to reflux for one hour. After cooling the red solid was separated by filtration, washed with water, and dried. There was thus obtained 4,6-diamino-2-[2-(4-methoxyphenyl)-ethyl]amino-5-nitrosopyrimidine (13.4 g, 84% yield). NMR: DMSO-$d^6$; 2.7–2.85(m,2H, C$H_2$—C$H_2$), 3.4–3.6(m, 2H, C$H_2$—NH), 3.7 (s, 3H, OC$H_3$), 6.75–6.8(m,2H, aromatic-$H$), 7.05–7.25 (m, 2H, aromatic-$H$) 7.4–10.5 (m,5H, N$H_2$×2, N$H$), m/e [M+H]$^+$ 289.

2) A mixture of 4,6-diamino-2-[2-(4-methoxyphenyl)-ethyl]amino-5-nitrosopyrimidine (13.3 g), absolute ethanol (150 ml) and water (150 ml) was heated almost to reflux. Sodium dithionite was added slowly, portionwise until the red colour disappeared. The mixture was filtered hot. After cooling the solid was removed by filtration, triturated with isopropyl alcohol, and dried to give 2-[2-(4-methoxyphenyl)ethyl]amino-4,5,6-triaminopyrimidine as a solid (8.2 g) m.p. 134°–138° C.; NMR: DMSO-$d^6$; 2.65–2.85(t, 2H, C$H_2$—CH$_2$), 3.25–3.5(t, 2H, C$H_2$–NH),3.7(s, 3H, OC$H_3$), 6.45–6.65 (b, 2H, N$H_2$), 6.7–6.85(b, 1H, N$H$), 6.8–6.9 (d,2H, aromatic-$H$), 7.1–7.25(d,2H, aromatic-$H$). Also 2.8–4.0 (v.br, 4H, 2×N$H_2$).

EXAMPLES 6–9

The following compounds of formula I were prepared by a method similar to that described in Example 4, but using the appropriate purine and methyl iodide.

EXAMPLE 6

6-Amino-8-(2-furyl)-2-[2-(4-methylphenyl)ethyl]amino-9-methyl-1H-purine; m.p. 158°–160° C.; NMR; DMSO-$d^6$; 2.2–2.3 (s, 3H, C$H_3$), 2.7–2.9 (m, 2H, C$H_2$—CH$_2$), 3.35–3.55 (m, 2H, C$H_2$NH), 3.8(s, 3H, NC$H_3$), 6.3 (t, 1H, N$H$CH$_2$), 6.7 (m,1H, furan —$H$), 6.7–6.8(b, 2H, N$H_2$), 7.0(d, 1H, furan-H), 7.05–7.2 (m, 4H, aromatic-$H$), 7.85–7.9 (d,1H, furan-$H$).

EXAMPLE 7

6-Amino-8-(2-furyl)-9-methyl-1H-purine; m.p. 260°–262° C.; microanalysis, found; C, 55.7; H, 4.3; N, 31.9%; $C_{10}H_9N_5O$ requires; C, 55.8; H, 4 2; N, 32.5%; NMR: DMSO-$d^6$; 3.9 (s,3H, C$H_3$), 6.75(m, 1H, furan-$H$), 7.2 (d, 1H, furan-H), 7.2–7.4 (b, 2H, N$H_2$), 7.95 (d, 1H, furan-$H$), 8.2 (s, 1H, N—C$H$—N).

EXAMPLE 8

6-Amino-2-benzylthio-8-(2-furyl)-9-methyl-1H-purine; m.p. 49°–152° C.; microanalysis, found; C, 59.3; H, 4.4; N, 19.9%; $C_{17}H_{15}N_5OS$, 0.5 $H_2O$ requires C, 59.0; H, 4.6; N, 20.2%; NMR; DMSO-$d^6$; 3.9 (s, 3H, N—C$H_3$), 4.4 (s, 2H, SC$H_3$), 4.4 (s, 2H, SC$H_2$), 6.7–6.8 (m, 1H, furan-$H$), 7.1–7.2 (d, 1H, furan-$H$), 7.2–7.55 (m, 7H, aromatic-$H$+N$H_2$), 7.95 (d, 1H, furan-$H$).

EXAMPLE 9

6-Amino-8-(2-furyl)-9-methyl-2-methylthio-1H-purine; m.p. >250° C.; microanalysis, found; C, 50.5; H, 4.1; N, 26.6%; $C_{11}H_{11}N_5OS$ requires; C, 50.6; H, 4.24; N, 26.8%; NMR: DMSO-$d^6$; 2.5(s, 3H, SC$H_3$), 3.8–3.9 (s, 3H, N—C$H_3$), 6.75(m, 1H, furan-$H$), 7.15 (d, 1H, furan-$H$), 7.3–7.5 (b, 2H, N$H_2$), 7.9–8.0 (d, 1H, furan-$H$).

EXAMPLES 10–14

The following compounds were prepared following the method described in Example 5, but using the appropriate triaminopyrimidine.

EXAMPLE 10

6-Amino-2-[2-(3,4-dimethoxyphenyl)ethyl]amino-8-(2-furyl)-1H-purine, m.p. 209° C. (with decomposition); found; C, 55.9; H, 5.4; N, 20.2%; $C_{19}H_{20}N_6O_3$ (1½ $H_2O$) requires; C, 56.0; H, 5.7; N, 20.6%; NMR; DMSO-$d^6$; 2.7–2.9 (t, 2H, C$H_2$—CH$_2$), 3.4–3.6(m,2H, C$H_2$NH), 3.37–3.8(d,6H,OC$H_3$×2), 6.6–6.7 (b, 1H, furan-$H$), 6.7–6.9 (m, 3H, aromatic-$H$), 7.0 (b, 1H, furan-$H$), 7.8–7.85(b, 1H, furan-H)>10( N$H$ and N$H_2$). m/e [M+H]$^+$ 381.

EXAMPLE 11

6-Amino-8-(2-furyl)-2-[2-(4-methylphenyl)ethyl]amino-1H-purine, m.p. 235°–237° C. (with decomposition); microanalysis, found; C, 59.2; H, 5.5; N, 21.4% $C_{18}H_{18}N_6O$. $0.5CH_3COOH$, $H_2O$ requires; C, 59.6; H, 5.5; N, 21.9%; NMR: DMSO-$d^6$ 1.85(s, 1 ½H, ½$CH_3$COOH), 2.25 (s,3H, $CH_3$), 2.7–2.9 (t, 2H, $CH_2$—$CH_2$), 3.4–3.55(q, 2H, NH$CH_2$), 6.1(t, 1H, NH), 6.65 (m, 2H, $NH_2$), 7.0 (d, 1H, furan-H), 7.05–7.2 (m, 4H, aromatic-H), 7.8 (m, furan-H).

EXAMPLE 12

6-Amino-8-(2-furyl)-2-[2-phenylethyl]amino-1H-purine, m.p. >240° C,; microanalysis, found; C, 61.4; H, 4.9; N, 25.2%; $C_{17}H_{16}N_6O$ (0.6 $H_2O$) requires; C, 61.7; H, 5.5; N, 25.3%; NMR: DMSO-$d^6$; 2.85 (m, 2H, $CH_2$Ph), 3.50 (m, 2H, $CH_2$NH), 6.1–6.25 (b, 1H, NH), 6.55–6.75(b, 3H, $NH_2$+furan-H), 6.95(d, 1H, furan-H), 7.15–7.4(m, 5H, aromatic H), 7.8(s, 1H, furan-H), 12.6 (b, 1H, NH).

EXAMPLE 13

6-Amino-2-benzylthio-8-(2-furyl)-1H-purine; m.p. 234° C. (with decomposition); microanalysis, found; C, 59.5; H, 4.1;. N, 21.3%; $C_{16}H_{13}N_5OS$ requires; C, 59.4; H, 4.1; N, 21.7%; NMR; DMSO-$d_6$; 4.3–4.4(s, 2H, $CH_2$—S), 6.7(m, 1H, furan H), 7.1(d, 1H, furan-H), 7.15–7.5 (m, 7H, aromatic-H+$NH_2$), 7.9 (d, 1H, furan-H), 13.1–13.4 (brs, 1H, NH).

EXAMPLE 14

6-Amino-8-(2-furyl)-2-methylthio-1H-purine; m.p. >250° C.; NMR; DMSO-$d^6$; 2.4–2.5 (s, 3H, S$CH_3$), 2.8–3.8 (br, 1H, NH), 6.7(d,1H, furan-H), 7.1 (d, 1H, furan-H), 7.1–7.25 (s, 2H, $NH_2$), 7.8–7.9(d, 1H, furan-H).

The starting materials for Examples 10, 11, 12 were prepared as described in Example 5 starting from 4,6-diamino-2-methylthio-5-nitrosopyrimidine. 4,6-diamino-2-(2-phenylethyl)amino-5-nitrosopyrimidine; m/e $[M+H]^{30}$ 259; 4,6-diamino-2-[2-(3,4-dimethyoxyphenyl)ethyl]amino-5-nitrosopyrimidine m/e $[M+H]^+$ 319; 4,6-diamino-2-[2-(4-methoxyphenyl)ethyl]amino-5-nitrosopyrimidine; 2-(2-phenylethyl)amino-4,5,6-triaminopyrimidine; m/e $[M+H]^+$ 245; 2-[2-(3,4-dimethoxyphenyl)ethyl]amino-4,5,6-triaminopyrimidine; m/e $[M+H]^+$ 305; and 2-[2-(4-methylphenyl)ethyl]amino-4,5,6-triaminopyrimidine; m/e $[M+H]^+$ 258.

EXAMPLE 15

A mixture of 4-amino-5-(2-furanylcarbonyl)amino-6-hydroxy-2-(2-phenyl)ethylpyrimidine (0.4 g) and phosphorus oxychloride (5 ml) was heated at reflux for 30 minutes. The excess phosphorus oxychloride was removed by distillation under reduced pressure followed by azeotroping with toluene (×2). The mixture was separated between chloroform and water. The organic layer was separated, dried and the solvent distilled off under reduced pressure. The solid produced was purified by flash column chromatography eluting with methanol/methylene chloride (3:97). There was thus produced 7-amino-2-(2-furyl)-5-(2-phenyl)ethyloxazolo[5,4-d]pyrimidine (0.18 g, 50% yield); m.p. 206°–208° C.; microanalysis, found: C, 66.0; H, 4.6; N, 18.2%; $C_{17}H_{14}N_4O_2$ (0.25$H_2O$) requires: C, 65.7; H, 4.7; N, 18.0%: NMR; DMSO-$d_6$; 2.9–3.15(m,4H, $CH_2$×2), 6.8(m, 1H, furan-H), 7.1–7.3 (m, 5H, aromatic-H), 7.35 (m, 1H, furan-H), 7.65–7.75 (b, 2H, $NH_2$), 6.0(m, 1H, furan-H).

The starting material was prepared as follows:- a) A mixture of sodium (0.25 g, 10.8 mM) and ethanol (30 ml) was stirred at ambient temperature under an argon atmosphere until all the metal had dissolved. 2-Phenylethylamidine hydrochloride (1.0 g, 5.43 mM) was added and the mixture stirred for 0.5 hours. Ethyl cyanoglyoxalate-2-oxime (0.77 g, 5.43 mM) was added and the mixture refluxed for 15 hours. After cooling, sodium ethoxide in ethanol (5.43 mM) was added and the mixture refluxed for a further 2.5 hours. After cooling, the solid produced was removed by filtration. The liltrate was distilled at reduced pressure and the residue triturated with hot water. The solid residue was crystallised from methanol/methylene chloride (8:92). There was thus obtained 4-amino-6-hydroxy-5-nitroso-2-(2-phenyl)ethylpyrimidine (1.9 g, 30% yield) NMR; DMSO-$d^6$; 2.65–2.85 (m, 2H, $CH_2$—$CH_2$), 2.85–3.1 (m,2H, $CH_2$—$CH_2$), 7.15–7.4 (m, 5H, aromatic-H), exchangeables under broad peaks.

b) A mixture of 4-amino-6-hydroxy-5-nitroso-2-(2-phenyl)-ethylpyrimidine (1.1 g, 4 mM), ethanol (15 ml) and water (35 ml) was heated to approx 60° C. Sodium dithionite was added slowly, portionwise until the green colour had disappeared. The mixture was then allowed to cool, concentrated to half the original volume, and cooled again. A pale beige precipitate was formed and was removed by filtration, washed with water, and dried. There was thus produced 4,5-diamino-6-hydroxy-2-(2-phenyl)ethylpyrimidine (0.7 g, 70% yield). NMR; DMSO-$d^6$; 2.6–2.8 (m, 2H, $CH_2$), 2.8–3.05(m, 2H, $CH_2$), 3.3–3.8(b, 2H, $NH_2$), 5.5(s, 2H, $NH_2$), 7.1–7.4 (m, 5H, aromatic-H), 11.4–11.75(b, 1H, OH).

c) To a mixture of 4,5-diamino-6-hydroxy-2-(2-phenyl)-ethylpyrimidine (0.55 g, 2.39 mM) and chloroform (40 ml) under an argon atmosphere, was added triethylamine (365μl, 2.63 mM) and then 2-furoyl chloride (258μl, 2.63mM) slowly over 0.25 hours. The mixture was stirred at ambient temperature for 15 hours. Water (50 ml) was then added. The organic layer was separated, and the solvent removed by distillation under reduced pressure. There was thus produced 4-amino-5-(2-furanylcarbonyl)amino-6-hydroxy-2-(2-phenyl)ethyl pyrimidine (0.6 g) as a solid; m.p. >240° C.: NMR: DMSO-$d^6$; 2.7 (m, 2H Ar-$CH_2$), 2.95(m, 2H, C$H_2$N), 6.2 (s, 2H, $NH_2$), 6.6 (m, 1H, furan-H), 7.3 (m, 1H, furan-H), 7.7(m, 5H, aromatic-H), 7.8 (m, 1H, furan-H), 8.7 (s, 1H, OH), 11.7 (b, 1H, NH—CO).

EXAMPLE 16

A mixture of 7-ethoxy-5-methyl-2-(2-furyl)-oxazolo[5,4-d] pyrimidine (0.6 g) and ethanol (saturated with ammonia) (20 ml) in a sealed tube was heated in an autoclave at 120° C. for 18 hours. After cooling, the solvent was distilled off under reduced pressure and the residue was purified by flash column chromatography, eluting with ethyl acetate/hexane (1:1), and was then further purified by flash column chromatography eluting with ammonia/methanol/methylene chloride (1:5:94). There was thus produced 7-amino-5-methyl-2-(2-furyl)-oxazolo[5,4-d]pyrimidine (0.25 g) m.p. 195°–196° C.; microanalysis, found; C,55.2; H, 3.6; N, 25.6%; $C_{10}H_8N_4O_2$ requires; C, 55.6; H, 3.7; N, 25 9%; NMR; DMSO-$d^6$; 2.4 (s, 3H, $CH_3$), 6.8 (m, 1H, furan-H), 7.3 (d, 1H, furan-H), 7.55–7.75 (b, 2H, $NH_2$), 8.0 (m, 1H, furan —H).

The starting material was prepared as follows:

a) A mixture of 5-carboxyethyl-4-ethoxy-2-(2-furyl)-oxazole (1.02 g, 4 mM) acetamidine nitrate (0.53 g, 4.4 mM), sodium carbonate (475 mg, 4.4 mM) and acetonitrile (30 ml) was heated at reflux for 4 hours. After cooling the mixture was concentrated. The residual syrup was dissolved in ethyl acetate and washed with dilute sodium hydroxide (3×50 ml). The aqueous extracts were combined, acidified with dilute hydrochloric acid and cooled. The resultant solid was filtered, washed with water and dried. There was thus produced 4-ethoxy-5-(2-furanylcarbonyl)amino-6-hydroxy-2-methylpyrimidine (0.5 g, 46% yield); microanalysis, found; C, 54.8; H, 5.1; N, 15.5%; $C_{12}H_{13}N_3O_4$ requires; C, 54.8; H, 5.0; N, 16.0%.

b) A mixture of 4-ethoxy-5-(2-furanylcarbonyl)amino-6-hydroxy-2-methylpyrimidine (2.07 g, 7.87 mM), phosphorus oxychloride (30 ml) and dimethylaniline (1.5 ml, 11.7 mM) was heated at reflux for one hour. After cooling, the excess phosphorus oxychloride was removed by distillation under reduced pressure. Ethanol was then added, and the mixture partitioned between methylene chloride and water. The organic layer was separated, washed with sodium bicarbonate, water, dilute hydrochloric acid, water, and dried. The solvent was then removed by distillation under reduced pressure. Ethanol (10 ml) was added and the solid filtered off. This solid was further purified by flash column chromatography eluting with ethyl acetate/hexane (1:3). There was thus produced 7-ethoxy-5-methyl-2-(2-furyl)-oxazolo[5,4-d]pyrimidine (1.49 g, 77% yield); m.p. 104°–105.5° C.

EXAMPLE 17

A mixture of 5-amino-4-cyano-2-(2-furyl)oxazole (2.33 g), cyanogen bromide (1.41 g), potassium cyanide (0.86 g), dimethylformamide (25 ml) and potassium t-butoxide (1.8 g) was stirred at 60° C. for 3 hours. The solvent was distilled off under reduced pressure and the residue purified by flash column chromatography eluting with ethyl acetate/hexane (40:60). The resultant solid was recrystallised from ethyl acetate/hexane. There was thus obtained 7-amino-5-cyano-2-(2-furyl)-oxazolo-[5,4-d]pyrimidine (75 mg); m.p. 260°–262° C.; microanalysis, found; C, 52.9; H, 2.2; N, 30.6%; $C_{10}H_5N_5O_2$ requires; C, 52.9; H, 2.2; N, 30.8%.

EXAMPLE 18

A mixture of 5-amino-4-cyano-2-(2-furyl)oxazole (190 mg, 1.1 mM), formamidine acetate (1.1 g, 11 mM) and dimethylformamide (10 ml) was heated at 100° C. under an atmosphere of argon for twenty minutes. The solvent was removed by distillation under reduced pressure and ethanol (5 ml) added to the residue. The solid was separated by filtration. There was thus obtained 7-amino-2-(2-furyl)oxazolo-[5,4-d]pyrimidine (0.19 g) m.p. >250° C.; microanalysis, found; C, 53.6; H, 2.8; N, 27.6%; $C_9H_6N_4O_2$ requires; C, 53.5; H, 3.0; N, 27.7%.

EXAMPLE 19

A mixture of 2-[2-(3,4-dimethoxyphenyl)ethyl]amino-4,5,6-triaminopyrimidine (0.5 g, 1.6 mM), furyl-2-glyoxal (0.2 g, 1.6 mM), ethanol (20 ml) and water (20 ml) was warmed at 60° C. for 0.5 hours. The solvents were removed by distillation under reduced pressure. The resultant syrup was purified by flash column chromatography eluting with methylene chloride containing slowly increasing amounts of methanol (0–6%). After removal of the solvent, a syrup was obtained and this was triturated with ethyl acetate and then methanol to give a solid. There was thus obtained 4-amino-2-[2-(3,4-dimethoxyphenyl)ethyl]amino-7-(2-furyl) pteridine (0.244 g) m.p. 200°–201° C.; microanalysis, found; C, 60.8; H, 5.3; N, 20.6; $C_{20}H_{20}N_6O_3+0.25 H_2O$ requires; C, 60.45; H, 5.2; N, 21.0%; NMR; DMSO-$d^6$; 2.75–2.9 (t, 2H, C$\underline{H}_2$—CH$_2$), 3.5–3.7 (q, 2H, C$\underline{H}_2$—NH), 3.7–3.8 (d, 6H, OC$\underline{H}_3$×2), 6.7–6.95(m, 4H, aromatic-H (×3)+furan-H), 6.95–7.1 (b, 1H, N$\underline{H}$), 7.35–7.65 (m,3H, NH$_2$+furan H), 8.0 (d, 1H, furan-$\underline{H}$), 8.65 (s, 1H, pteridine-H); m/e [M+H]$^+$ 393.

EXAMPLES 20–22

The following compounds were prepared by a method similar to that described in Example 19, but using the appropriate triaminopyrimidine:

EXAMPLE 20

4-amino-2-[2-(4-methoxyphenyl)ethyl]amino-7-(2-furyl)-pteridine; m.p 210°–214° C. (with decomposition); NMR; DMSO-$d^6$; 2.75–2.95 (t, 2H, C$\underline{H}_2$—CH$_2$), 3.45–3.65(q, 2H, C$\underline{H}_2$NH), 3.7 (s, 3H, OC$\underline{H}_3$), 6.7 (m, 1H, furan-$\underline{H}$), 6.8–6.9 (d, 2H, aromatic-$\underline{H}$), 7.0–7.1 (b, 1H, N$\underline{H}$), 7.1–7.2 (d, 2H, aromatic-$\underline{H}$), 7.35–7.5 (b, 1H, furan-$\underline{H}$), 7.5–7.65 (b, 2H, N$\underline{H}_2$), 8.0 (s, 1H, furan-$\underline{H}$), 8.65 (s, 1H, pteridine-$\underline{H}$). m/e [M+H]$^+$ 363.

EXAMPLE 21

4-amino-2-[2-(4-methylphenyl)ethyl]amino-7-(2-furyl)-pteridine; m.p. 153°–154° C.; NMR; DMSO-$d^6$; 2.3(s, 3H, C$\underline{H}_3$) 2.85–2.95(t, 2H, C$\underline{H}_2$—CH$_2$), 3.65–3.75(t, 2H, C$\underline{H}_2$NH), 6.75 (m, 1H, furan $\underline{H}$), 7.1–7.25(q, 4H, aromatic-H), 7.5 (d, 1H, furan-$\underline{H}$), 7.8–8.2 (b, 3H, N$\underline{H}_2$+furan-$\underline{H}$), 8.8 (s,1H, pteridine-$\underline{H}$); m/e [M+H]$^+$ 347.

EXAMPLE 22

4-Amino-2-methylthio-7-(2-furyl)pteridine. m.p. >250° C.; NMR; DMSO-$d^6$; 2.55 (s,3H, SC$\underline{H}_3$), 6.8(m, 1H, furan-$\underline{H}$), 7.6 (d, 1H, furan-$\underline{H}$), 8.05 (m, 1H, furan-$\underline{H}$), 8.1–8.25 (b, 2H, N$\underline{H}_2$), 9.0 (s, 1H, pteridine-$\underline{H}$); m/e [M+H]$^+$ 260.

EXAMPLE 23

A mixture of 2-[2-(3,4-dimethoxyphenyl)ethyl]amino-4,5,6-triaminopyrimidine (1.0 g, 3.2 mM), furyl-2-glyoxol (0.4 g, 3.2 mM), ethanol (30 ml) and 2M sulphuric acid (30ml) was heated at 60° C. for 1.5 hours. After cooling the solution was adjusted to PH 14 using dilute sodium hydroxide solution. The mixture was then extracted with ethyl acetate. The organic extracts were combined, dried, the solvent evaporated under reduced pressure. The resultant solid was triturated with methanol. There was thus produced 4-amino-2-[2-(3,4-dimethoxyphenyl)ethyl]amino-6-(2-furyl)-pteridine (0.85 g) m.p. 178°–180° C.; microanalysis, found; C, 59.1; H, 4.9; N, 20.7%; $C_{20}H_{20}N_6O_3$ +0.75 H$_2$O requires; C, 59.1; H, 5.17; N, 20.7; NMR; DMSO-$d^6$; 2.75–2.9 (t, 2H, C$\underline{H}_2$—CH$_2$), 3.5–3.7 (b, 2H, C$\underline{H}_2$—NH), 3.7–3.8 (d, 6H, OC$\underline{H}_3$×2), 6.7 (m, 1H, furan-$\underline{H}$), 6.7–6.9 (m, 3H, aromatic-$\underline{H}$), 7.1 (b, 1H, N$\underline{H}$), 7.3 (d, 1H, furan-$\underline{H}$), 7.5–7.7 (b, 2H, N$\underline{H}_2$), 7.85 (d, 1H, furan-$\underline{H}$), 9.05 (s, 1H, pteridine-$\underline{H}$); m/e [M+H]$^+$ 393.

EXAMPLES 24-26

The following compounds were prepared by a method similar to that described in Example 23 but using the appropriate triaminopyrimidine:-

EXAMPLE 24

Preparation worked up without basification. There was thus produced 4-amino-2-[2-(4-methylphenyl)ethyl]amino-6-(2-furyl)-pteridine m.p. 246°–248° C. (with decomposition); microanalysis; found; C, 46.2; H, 4.0; N, 16.4; S, 9.8%; $C_{19}H_{18}N_6O+1.5H_2SO_4$ requires; C, 46.2; H, 4.3; N, 17.0; S, 9.8%; NMR: DMSO-$d^6$; 2.3(s,3H, C$\underline{H}_3$), 2.8–2.95(m, 2H, C$\underline{H}_2$—CH$_2$), 3.6–3.8 (b, 2H, C$\underline{H}_2$NH), 6.8 (m, 1H, furan-$\underline{H}$), 7.05–7.25(m, 4H, aromatic-H), 7.5 (d, 1H, furan-$\underline{H}$), 7.9–8.0 (b, 1H, furan-$\underline{H}$), 8.8–9.0 (b, 1H, N$\underline{H}$), 9.2 (b, 1H, pteridine-$\underline{H}$), 9.25–9.6 (b, 2H, N$\underline{H}_2$). m/e [M+H]$^+$ 347.

EXAMPLE 25

4-Amino-2-[2-(4-methoxyphenyl)ethyl]amino-6-(2-furyl)-pteridine; m.p. 212°–214° C.; NMR: DHSO-$d^6$; 2.75–2.9 (t, 2H C$\underline{H}_2$—CH$_2$) 3.45–3.6 (q, 2H, C$\underline{H}_2$NH), 3.7 (s, 3H, OC$\underline{H}_3$), 6.7 (m, 1H, furan-$\underline{H}$), 6.6–6.7 (d, 2H, aromatic-$\underline{H}$), 7.1 (b, 1H, N$\underline{H}$), 7.15–7.25 (d, 2H, aromatic-$\underline{H}$), 7.3 (d, 1H, furan-$\underline{H}$), 7.5–7.7 (b, 2H, N$\underline{H}_2$), 7.85 (m, 1H, furan-$\underline{H}$), 9.05 (s, 1H, pteridine-$\underline{H}$). m/e [M+H]$^+$ 363.

EXAMPLE 26

4-Amino-2-methylthio-6-(2-furyl)-pteridine; m.p. 200° C.; microanalysis; found; C, 49.5; H, 3.6; N, 25.7%; $C_{11}H_9N_5O$ S (0.5H$_2$O) requires; C, 49.3; H, 3.7; N, 26.1%; NMR: DMSO-$d^6$; 2.55 (s 3H, SC$\underline{H}_3$) 6.75 (m, 1H, furan-$\underline{H}$), 7.5 (d, 1H, furan-$\underline{H}$), 7.95 (d, 1H, furan-$\underline{H}$) 8.1–8.4 (b, 2H, N$\underline{H}_2$), 9.3 (s, 1H, pteridine-$\underline{H}$).

EXAMPLE 27

The following illustrate representative pharmaceutical dosage forms containing a compound of formula I, for example as illustrated in any of the previous Examples, (hereafter referred to as "compound X"), for therapeutic or prophylactic use in humans:-

| (a) Tablet | mg/tablet |
| --- | --- |
| Compound X | 50 |
| Lactose Ph.Eur | 223.75 |
| Croscamellose sodium | 6.0 |
| Maize starch | 15.0 |
| Polyvinylpyrrolidone (5% w/v paste) | 2.25 |
| Magnesium stearate | 3.0 |

| (b) Capsule | mg/capsule |
| --- | --- |
| Compound X | 10 |
| Lactose Ph.Eur | 488.5 |
| Magnesium stearate | 1.5 |

The above formulations may be obtained by conventional procedures well known in the pharmaceutical art. The tablets may be enteric coated by conventional means, for example to provide a coating of cellulose acetate phthalate.

CHEMICAL FORMULAE

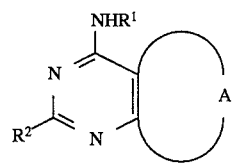

I

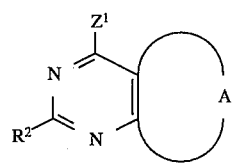

II

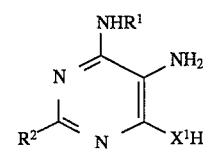

III

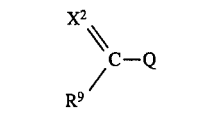

IV

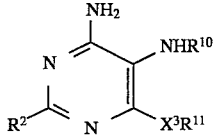

V

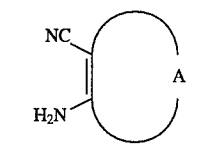

VI

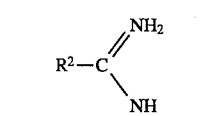

VII

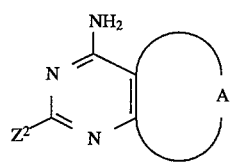

VIII

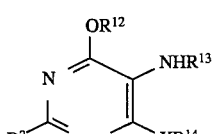

IX

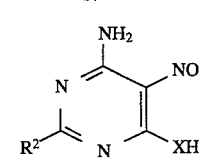

X

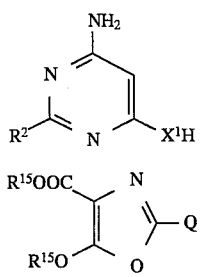

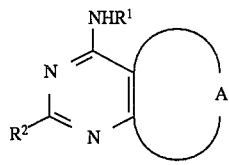

What is claimed is:
1. A compound of the formula I wherein:

![formula I]

$R^1$ is hydrogen, (1–6C)alkyl, or (1–4C)alkanoyl;

$R^2$ is hydrogen, cyano or a group of formula $R^3X$;

$R^3$ (when not as hereinbelow defined together with X) is (3–12C)cycloalkyl, (3–6C)alkenyl, phenyl(3–6C)alkenyl, 5- or 6-membered heteroaryl, optionally substituted (1–6C)alkyl or optionally substituted phenyl, said optionally substituted alkyl being unsubstituted or substituted by one of (3–6C)cycloalkyl, optionally substituted 5- or 6-membered heteroaryl, optionally substituted phenyl and a group of formula $R^4(CO)_nX_a(CO)_m$ in which $R^4$ is (1–6C)alkyl, (3–6C)cycloalkyl, optionally substituted phenyl or optionally substituted phenyl(1–4C)alkyl, n and m are each 0 or 1, provided that n+m is 0 or 1, and that when m is 0, X and $X_a$ are separated by at least two carbon atoms, $X_a$ is oxy, thio, sulphinyl, sulphonyl or an imino group of formula —NRb in which Rb is hydrogen, (1–6C)alkyl or together with $R^4$ and the adjacent nitrogen atom forms a 4 to 6-membered saturated heterocyclic ring, said optionally substituted 5- or 6-membered heteroaryl being unsubstituted or substituted by 1 or 2 of (1–4C)alkyl, (1–4C)alkoxy and halogeno, and any of said optionally substituted phenyl being unsubstituted or substituted by (1–4C)alkylenedioxy or by 1,2 or 3 of halogeno, cyano, trifluoromethyl, (1–4C)alkoxycarbonyl, hydroxy, hydroxymethyl, amino, (1–4C)alkanoylamino, (1–4C)alkoxymethyl, (1–4C)alkanoyloxy, benzyloxy, halogenobenzyloxy, (1–4C)alkylsulphonylamino, (1–4C)haloalkylsulphonylamino, nitro, and (1–4C)alkyl or alkoxy optionally bearing a group of formula $R^5CO$ in which $R^5$ is (1–4C)alkoxy, (3–6C)alkylamino, (3–6C)cycloalkylamino or (N-(1–4C)alkyl) (N-(1–4C) dialkylamino(1–4C)alkyl)amino, and sulphamoyl of formula —$SO_2.NR^6R^7$ in which $R^6$ and $R^7$ are independently hydrogen or (1–4C)alkyl, or $R^6$ is hydrogen and $R^7$ is ((2–5C)alkoxycarbonyl)-$(CH_2)_q$—, carbamoyl$(CH_2)q$ or (N-(1–4C)alkylcarbamoyl) $(CH_2)q$, in which q is 0 or an integer of from 1 to 4 or $R^6$ is (1–4C)alkyl and $R^7$ is di(1–4C)alkylamino(1–4C)alkyl; and X is a direct bond or oxy, thio, sulphinyl, sulphonyl or an imino group of formula —NRa— in which Ra is hydrogen, (1–6C)alkyl or together with $R^3$ and the adjacent nitrogen atom forms a 4 to 6-membered saturated heterocyclic ring;

A is —N=CQ—$NR^8$—;

Q is 2-furyl; and $R^8$ is hydrogen or (1–4C)alkyl; provided that when $R^1$ and $R^2$ are hydrogen and A is —N=CQ—$NR^8$—, $R^8$ is not hydrogen; or a pharmaceutically acceptable salt thereof.

2. A compound as claimed in claim 1, in which $R^1$ is hydrogen.

3. A compound as claimed in claim 1, in which said 5- or 6-membered heteroaryl represented by $R^3$ is selected from pyridyl, isoxazolyl and thiadiazolyl, and the 5- or 6-membered heteroaryl in said optionally substituted 5- or 6-membered heteroaryl is selected from furyl, pyridyl and thienyl.

4. A compound as claimed in claim 1 or claim 2, in which $R^2$ is hydrogen, cyano or $R^3X$ in which $R^3$ is (1–4C)alkyl, (3–6C)alkenyl, pyridyl(1–4C)alkyl or phenyl(1–4C)alkyl optionally substituted on the phenyl moiety by 1 or 2 of halogen, hydroxy, (1–4C)alkanoyloxy, (1–4C)alkyl and (1–4C)alkoxy; and X is a direct bond, oxy, thio or NH.

5. A compound as claimed in claim 4, in which $R^2$ is 4-chlorobenzyl, 2-phenylethyl, 2-phenylethylamino, 2-(4-hydroxy-phenyl)ethylamino, 2-(4-methylphenyl)ethylamino, 2-(4-methoxyphenyl)-ethylamino or 2-(3,4-dimethoxyphenyl)ethylamino.

6. A compound as claimed in claim 1 or claim 2, in which $R^8$ is hydrogen or methyl.

7. A compound as claimed in claim 1, in which $R^1$ is hydrogen;

$R^2$ is $R^3X$ $R^3$ is (1–4C)alkyl, (3–6C)alkenyl, pyridyl(1–4C)alkyl or phenyl(1–4C)alkyl optionally substituted on the phenyl moiety by 1 or 2 of halogen, hydroxy, (1–4C)alkanoyloxy, (1–4C)alkyl and (1–4C)alkoxy;

X is a direct bond, oxy, thio or NH;

A is —N=CQ—$NR^8$—;

Q is 2-furyl; and $R^8$ is hydrogen or methyl.

8. A pharmaceutical composition, which comprises a compound of formula I or a pharmaceutically acceptable salt thereof as defined in claim 1, in a mixture or together with a pharmaceutically acceptable diluent or carrier.

9. A method of antagonising one or more of the actions of adenosine in a warm-blooded animal requiring such treatment by administering an effective amount of a compound of formula I as defined in claim 1, or a pharmaceutically acceptable salt thereof.

* * * * *